United States Patent
Derez et al.

(10) Patent No.: US 10,851,183 B2
(45) Date of Patent: *Dec. 1, 2020

(54) HYDROLYZED STARCH COMPOSITIONS AND THEIR USE IN FOOD APPLICATIONS

(71) Applicant: CARGILL, INCORPORATED, Wayzata, MN (US)

(72) Inventors: Frank Derez, Sint-Pieters-Leeuw (BE); Baljit S. Ghotra, Wayzata, MN (US); John R. Heigis, Cedar Rapids, IA (US); John Zupfer, Moundsview, MN (US)

(73) Assignee: Cargill, Incorporated, Wayzata, MN (US)

( * ) Notice: Subject to any disclaimer, the term of this patent is extended or adjusted under 35 U.S.C. 154(b) by 26 days.

This patent is subject to a terminal disclaimer.

(21) Appl. No.: 15/915,323

(22) Filed: Mar. 8, 2018

(65) Prior Publication Data

US 2018/0255817 A1    Sep. 13, 2018

Related U.S. Application Data

(60) Provisional application No. 62/469,780, filed on Mar. 10, 2017.

(51) Int. Cl.
| | |
|---|---|
| *C08B 31/00* | (2006.01) |
| *A23L 29/00* | (2016.01) |
| *A23L 29/212* | (2016.01) |
| *A23L 29/219* | (2016.01) |
| *A23C 9/13* | (2006.01) |
| *A23C 13/12* | (2006.01) |
| *A23L 29/30* | (2016.01) |
| *C12N 9/26* | (2006.01) |
| *C12P 19/14* | (2006.01) |

(52) U.S. Cl.
CPC ............ *C08B 31/00* (2013.01); *A23C 9/13* (2013.01); *A23C 13/12* (2013.01); *A23L 29/00* (2016.08); *A23L 29/03* (2016.08); *A23L 29/212* (2016.08); *A23L 29/219* (2016.08); *A23L 29/35* (2016.08); *C12N 9/2414* (2013.01); *C12P 19/14* (2013.01); *A23C 2240/15* (2013.01); *A23V 2002/00* (2013.01); *A23V 2250/5118* (2013.01); *A23V 2300/28* (2013.01)

(58) Field of Classification Search
CPC ... A23L 29/212; A23L 29/035; A61K 31/718; A61K 31/702
USPC .......................................................... 536/45
See application file for complete search history.

(56) References Cited

U.S. PATENT DOCUMENTS

2012/0121873 A1* 5/2012 Mann ..................... C09J 103/00
428/211.1

FOREIGN PATENT DOCUMENTS

| | | | |
|---|---|---|---|
| CN | 106318991 A | * | 1/2017 |
| WO | WO 20170098191 | | 6/2017 |

OTHER PUBLICATIONS

Ba et al. (European Food Research & Technology, 2013, pp. 1-25).*
Onishi et al.; JP 59205965 A; Nov. 21, 1984 ( Machine-English Translation).*
Dou et al.; CN 106318991 A; Jan. 11, 2017 (Machine-English Translation).*
Yangcheng et al. (J. Agric. Food Chem. 2013, 61, 379-386).*

* cited by examiner

*Primary Examiner* — Shaojia A Jiang
*Assistant Examiner* — Michael C Henry

(57) ABSTRACT

Provided herein are common starch-based and waxy starch-based hydrolyzed starches. The hydrolyzed starches described herein demonstrate desirable properties over existing hydrolyzed starches for food applications, including but not limited to, dairy, ready-to-eat cereal coatings, clean-label confectionary products, nutritional and cereal bars, crumb chocolate, infant and/or elderly nutrition.

16 Claims, No Drawings

HYDROLYZED STARCH COMPOSITIONS AND THEIR USE IN FOOD APPLICATIONS

CROSS-REFERENCE TO RELATED APPLICATIONS

This application claims priority to U.S. Provisional Application 62/469,780, filed on Mar. 10, 2017, which is hereby incorporated by reference.

TECHNICAL FIELD

This disclosure relates to hydrolyzed starches, the process for manufacturing hydrolyzed starches, and their use in food applications.

BACKGROUND

Starch is a common food ingredient used in both food and non-food applications. Hydrolyzed starches are the dried products or aqueous dispersions of saccharides (hydrolysates) obtained by hydrolysis of native starch by using suitable acid or enzymes. Certain such hydrolyzed starches may be referred to as "maltodextrins." They are typically categorized having a dextrose equivalent (DE) of less than 20. DE is defined as the percentage of reducing sugar calculated as dextrose on a dry weight basis. Hydrolyzed starches are desirable for food applications because they extend the technical use of starch in many food and non-food applications. Hydrolyzed starches offer unique functional properties in food, label-friendly options, superior mouth feel and taste, and cost effectiveness when compared to other hydrocolloid systems.

BRIEF SUMMARY

Provided herein are common starch-based and waxy starch-based hydrolyzed starches having a range of DE values, such as 1, 5, 10, and 18. The hydrolyzed starches described herein are obtained through an enzymatic hydrolysis technique using, for example, alpha-amylases such as DSM's Maxamyl™ HT Ultra. In some aspects, the hydrolyzed starches described herein demonstrate desirable properties over certain hydrolyzed starches of the prior art for food applications, such as, but not limited to, dairy, ready-to-eat cereal coatings, clean-label confectionary products, nutritional and cereal bars, crumb chocolate, infant nutrition, and/or elderly nutrition.

DETAILED DESCRIPTION

Hydrolyzed Starch Compositions

To obtain the hydrolyzed starches of the present invention a variety of starting starch materials can be used. In certain aspects, the starting starch materials may be corn/maize starch, potato starch, tapioca starch, pulse starch (including but not limited to pea starch), and rice starch. Other suitable starting starch materials may be sweet potato starch, wheat starch, mung bean starch, oat and barley starch. Such starting starch materials may come from regular starch crops or mutant starch crops. Regular starch, also known as "non-mutant" or "common" starch, is made up of two components—amylose and amylopectin, which range from 20-30% and 70-80%, respectively, of the total starch. Amylose is mainly a linear polymer consisting of α-(1→4) linked D-Glucopyranosyl units, whereas amylopectin is a branched polymer consisting of linear α-(1→4) linked D-Glucopyranosyl units with α-(1→6) linked D-Glucopyranosyl branch chains. Distinguishable from common starch, mutant starch varieties known in the art may include waxy type or high amylose type hybrids. Waxy starches are made primarily (nearly 100%) of an amylopectin component whereas high amylose mutants typically contain a high content of amylose, usually upwards of 40% amylose. Certain such mutant starch varieties are known in the art and may be derived from different botanical sources such as, corn, potato, wheat, barley, tapioca, etc.

Utilizing the methods described herein, a variety of hydrolyzed starch compositions, derived from waxy and/or common starch materials, may be achieved, which demonstrate superior performance over hydrolyzed starches of the prior art.

The hydrolyzed starches described herein are of various dextrose equivalent (DE) values ranging from 0 to 20, such as, for example, DE0-3, DE3-8, DE8-14, or DE14-20, and DE 1, DE 5, DE 10, and DE 18. The hydrolyzed starches may be derived from waxy and/or common starch. In some aspects, the hydrolyzed starches are derived from waxy corn starch and/or or common corn starch. In some aspects, the hydrolyzed starches described herein have desirable gelling properties. In some aspects, the hydrolyzed starches described herein have reduced viscosity, which may allow for easier and more efficient in-process handling, dispensing, and pumping. In some aspects, the hydrolyzed starches described herein have an opaque clarity. In some such aspects, the hydrolyzed starches described herein may be particularly useful in dairy food applications. In some aspects, the hydrolyzed starches described herein have reduced molecular weights compared to prior art hydrolyzed starches. In some such aspects, the hydrolyzed starches described herein are more easily digestible, and may be particularly useful in infant and elderly nutrition.

Exemplary Waxy Starch-Based Hydrolyzed Starches

In some aspects, a hydrolyzed starch composition provided herein is derived from waxy starch. In some aspects, the hydrolyzed starch composition is obtained from waxy starch using an alpha-amylase such as DSM's Maxamyl™ HT Ultra. In some aspects, such a hydrolyzed starch composition derived from waxy starch has a dextrose equivalent (DE value) of greater than 0 to 3, such as 0.5 to 3, or 1 to 2, or about 1.5. In some aspects, the hydrolyzed starch composition with a DE value of greater than 0 to 3 (i) has a degree of polymerization (DP) between 46-6172 of >80%, and/or (ii) has an average molecular weight (mw) of <500 kDa, and/or (iii) forms a gel at 30% solids in aqueous medium. In some aspects, the hydrolyzed starch composition has a degree of polymerization (DP) between 46-6172 of 80-95%. In some aspects, the hydrolyzed starch composition has an opaque clarity indicated by a Hunter L value of >30, >40, >50, >60, >70, or >80. In some aspects, the hydrolyzed starch composition has an opaque clarity indicated by a Hunter L value of 30-100, or 40-100, or 50-100, or 60-100, or 70-100. In some aspects, the hydrolyzed starch composition has a gel strength at 30% solids in aqueous medium of >300 g, >400 g, >500 g, >600 g, >700 g, or >800 g, or 300-2000 g, or 500-2000 g, or 500-1500 g. In some aspects, the hydrolyzed starch has a lower average molecular weight than a hydrolyzed starch with a similar DE produced by hydrolyzing waxy starch with α-amylase GC100 (Genencor). In some instances, a hydrolyzed starch with a similar DE produced by hydrolyzing waxy starch with α-amylase GC100 does not form a gel at 30% solids in aqueous medium.

In some aspects, a hydrolyzed starch composition derived from waxy starch has a dextrose equivalent (DE value) of 3 to 9, such as 4 to 9, or 5 to 9, or 6 to 9, or 7 to 9. In some aspects, the hydrolyzed starch composition with a DE value of 3 to 9 (i) has a degree of polymerization (DP) between 10-45 of >40%, and/or (ii) an average molecular weight (mw) of <60 kDa. In some aspects, the DP of hydrolyzed starch between 10-45 is >50%, or >60%, or 40-95%, 40-90%, 50-90%, 55-90%, 60-90%, 60-80%. In some aspects, the average mw of the hydrolyzed starch is <50 kDa, or <40 kDa. In some aspects, the hydrolyzed starch composition forms a gel at 30% solids in aqueous medium. In some aspects, the composition has an opaque clarity indicated by a Hunter L value of >30, >40, >50, >60, >70, or 30-90, 40-90, 50-90, or 60-90. In some aspects, the hydrolyzed starch composition is obtained from waxy starch using an alpha-amylase such as DSM's Maxamyl™ HT Ultra. In some aspects, the hydrolyzed starch has a lower average molecular weight and/or a higher percentage of hydrolyzed starches with a DP between 10-45 than a hydrolyzed starch with a similar DE produced by hydrolyzing waxy starch with α-amylase GC100 (Genencor). In some aspects, a hydrolyzed starch with a similar DE produced by hydrolyzing waxy starch with α-amylase GC100 does not form a gel at 30% solids in aqueous medium.

In some aspects, a hydrolyzed starch composition derived from waxy starch has a dextrose equivalent (DE value) of 9 to 14, or 9 to 13, or 11 to 14. In some aspects, the hydrolyzed starch composition with a DE of 11 to 14 (i) has a degree of polymerization (DP) between 10-45 of >40%, and/or (ii) an average molecular weight (mw) of <35 kDa. In some aspects, the DP of the hydrolyzed starch between 10-45 is >50% or >60%. In some aspects, the DP of the hydrolyzed starch between 10-45 is 40-95%, 50-95%, or 60-95%. In some aspects, the average mw of the hydrolyzed starch is <30 kDa, <25 kDa, <20 kDa, or 2-20 kDa, 5-20 kDa, or 5-15 kDa. In some aspects, the hydrolyzed starch composition is obtained from waxy starch using an alpha-amylase such as DSM's Maxamyl™ HT Ultra. In some aspects, the hydrolyzed starch has a lower average molecular weight and/or a higher percentage of hydrolyzed starches with a DP between 10-45 than a hydrolyzed starch with a similar DE produced by hydrolyzing waxy starch with α-amylase GC100.

In some aspects, a hydrolyzed starch composition derived from waxy starch has a dextrose equivalent (DE value) of 14 to 20, or 16 to 20. In some aspects, the hydrolyzed starch composition with a DE of 14 to 20 (i) has a degree of polymerization (DP) between 6-45 of >60%, and/or (ii) an average molecular weight (mw) of <10 kDa. In some aspects, the hydrolyzed starch has an average mw of <8 kDa, <7 kDa, <6 kDa, 1-10 kDa, 1-8 kDa, 1-7 kDa, or 1-6 kDa. In some aspects, the hydrolyzed starch has a DP between 6-45 of >70%, >80%, 60-95%, 70-95%, or 80-95%. In some aspects, the hydrolyzed starch has a DP between 1-45 of >80% or >90%, or 80-99%, or 90-99%. In some aspects, the hydrolyzed starch composition is obtained from waxy starch using an alpha-amylase such as DSM's Maxamyl™ HT Ultra. In some aspects, the hydrolyzed starch has a lower average molecular weight and/or a higher percentage of hydrolyzed starches with a DP between 1-45 than a hydrolyzed starch with a similar DE produced by hydrolyzing waxy starch with α-amylase GC100. In some aspects, the waxy starch is waxy corn starch.

In various aspects, the hydrolyzed starch may be derived from corn starch, potato starch, tapioca starch, pea starch, legume starch, or rich starch.

Exemplary Common Starch-Based Hydrolyzed Starches

In some aspects, a hydrolyzed starch composition provided herein is derived from common starch. In some aspects, the hydrolyzed starch composition is obtained from common starch using an alpha-amylase such as DSM's Maxamyl™ HT Ultra. In some aspects, such a hydrolyzed starch composition derived from common starch has a dextrose equivalent (DE value) of greater than 0 to 3, such as 0.5 to 3, or 1 to 2, or about 1.5. In some aspects, the hydrolyzed starch composition with a DE value of greater than 0 to 3 (i) has a degree of polymerization (DP) between 601-6172 of >40%, and/or (ii) has an average molecular weight (mw) of <3500 kDa. In some aspects, the hydrolyzed starch has a DP between 601-6172 of 40-70% and an average mw of 1000-3500 kDa. In some aspects, the hydrolyzed starch composition has a viscosity of >1000 cp, or 1000-2000 cp, or >1200 cp, or 1200-2000 cp, at 95° C. at 200 s$^{-1}$. In some aspects, the hydrolyzed starch composition has a viscosity of >3000 cp, >4000 cp, or >5000 cp, or 3000-8000 cp, 4000-8000 cp, or 5000-8000 cp, at 50° C. at 200 s$^{-1}$. In some aspects, the hydrolyzed starch with a DP between 601-6172 is >45%, or 45-70%. In some aspects, the hydrolyzed starch has a lower average molecular weight and/or a higher percentage of hydrolyzed starches with a DP between 601-6172 than a hydrolyzed starch with a similar DE produced by hydrolyzing common starch with α-amylase GC100 (Genencor).

In some aspects, a hydrolyzed starch composition derived from common starch has a dextrose equivalent (DE value) of 3 to 8, such as 3 to 6 or 4 to 6. In some aspects, the hydrolyzed starch composition with a DE value of 3 to 8 (i) has a degree of polymerization (DP) between 10-125 of >20%, and/or (ii) has an average molecular weight (mw) of <300 kDa. In some aspects, the DP of the hydrolyzed starch is between 10-125 is >30%, >40%, or >50%, or 20-80%, 30-80%, 40-80%, or 50-80%. In some aspects, the average mw of the hydrolyzed starch is <200 kDa, or 20-300 kDa, or 20-200 kDa, or 20-150 kDa. In some aspects, the hydrolyzed starch composition forms a gel at 30% solids with a viscosity of <10 cp at 95° C. at 200 s$^{-1}$, and/or <40 cp or 15-40 cp at 50° C. at 200 s$^{-1}$, and/or <100 cp or 40-100 cp or 40-90 cp at 20° C. at 1000 s$^{-1}$. In some aspects, the hydrolyzed starch has a lower average molecular weight and/or a higher percentage of hydrolyzed starches with a DP between 10-125 than a hydrolyzed starch with a similar DE produced by hydrolyzing common starch with α-amylase GC100. In some aspects, the hydrolyzed starch forms a gel with a lower viscosity than a hydrolyzed starch with a similar DE produced by hydrolyzing common starch with α-amylase GC100.

In some aspects, a hydrolyzed starch composition derived from common starch has a dextrose equivalent (DE value) of 8 to 14, such as 8 to 12. In some aspects, the hydrolyzed starch composition with a DE value of 8 to 14 (i) has a degree of polymerization (DP) between 10-125 of >30%, and/or (ii) has an average molecular weight (mw) of <40 kDa. In some aspects, the DP between 10-125 is >40%, >50%, >60%, or >70%, or 30-95%, 40-95%, 50-95%, 60-95%. In some aspects, the average mw of the hydrolyzed starch is <30 kDa, or 5-40 kDa, or 5-30 kDa. In some aspects, the hydrolyzed starch composition forms a gel at 30% solids in aqueous medium. In some aspects, the hydrolyzed starch composition has an opaque clarity indicated by a Hunter L value of >50, >60, >70, or >80, or 50-100, 60-100, 70-100, 80-100, or 85-99. In some aspects, the hydrolyzed starch has a lower average molecular weight and/or a higher percentage of hydrolyzed starches with a DP between 10-125 than a hydrolyzed starch with a similar DE produced by hydrolyzing common starch with α-amylase GC100.

In some aspects, a hydrolyzed starch composition derived from common starch has a dextrose equivalent (DE value) of 14 to 20, such as 15 to 20 or 16 to 20. In some aspects, the hydrolyzed starch composition with a DE value of 14 to 20 has an average molecular weight (mw) of <20 kDa or <10 kDa, or 1-15 kDa, or 1-12 kDa, or 1-10 kDa, or 2-10 kDa. In some aspects, the composition has an opaque clarity indicated by a Hunter L value of >50, or >60, or 50-90, or 50-80, or 60-80. In some aspects, the hydrolyzed starch has a lower average molecular weight than a hydrolyzed starch with a similar DE produced by hydrolyzing common starch with α-amylase GC100.

In various aspects, the hydrolyzed starch may be derived from corn starch, potato starch, tapioca starch, pea starch, legume starch, or rich starch. In some aspects, the common starch of the hydrolyzed starch composition is common corn starch.

Process for Manufacturing Hydrolyzed Starch

One skilled in the art will appreciate that the commercial production of hydrolyzed starches includes the steps of (1) liquefaction (gelatinization or solubilization of starch); (2) saccharification (hydrolysis, specific DE attainment); (3) clarification (removal of insoluble); (4) optionally refining using a carbon column or ion exchange resin; (5) evaporation to increase solids concentration; and (6) liquid hydrolyzed starch load-out or spray drying. A more detailed description of an exemplary process for making the hydrolyzed starch compositions provided herein may be found in the Examples section.

There are many ways to complete the hydrolysis step. The hydrolyzed starch compositions described herein may be achieved, for example, through an enzymatic hydrolysis techniques utilizing alpha-amylases such as DSM's Maxamyl™ HT Ultra Potential End-Use Applications The various aspects of hydrolyzed starch compositions described herein can be used in a variety of food applications, including but not limited to, dairy, ready-to-eat cereal coatings, clean-label confectionary products, nutritional and cereal bars, crumb chocolate, infant nutrition, and/or elderly nutrition.

In some aspects, a hydrolyzed starch composition provided herein is used in dairy applications. Nonlimiting exemplary such dairy applications include yogurt and sour cream. In some aspects, a hydrolyzed starch composition provided herein having a DE of >0 to 3 is particularly suitable for such dairy applications. Some such hydrolyzed starches provided herein have high viscosity at both higher and lower temperature and shear, making them particularly suitable for dairy applications, such as dairy applications involving homogenization. For example, sour cream made using a 1DE common starch-derived hydrolyzed starch described herein demonstrated good structure and a smooth, shiny appearance compared to sour cream made using a control 1DE common starch-derived hydrolyzed starch, which had weaker structure. Similarly, yogurt made using a 1DE common starch-derived hydrolyzed starch described herein demonstrated good body and texture, while yogurt made using a control 1DE common starch-derived hydrolyzed starch had too think body and unacceptable texture.

Certain hydrolyzed starches provided herein comprise lower degrees of polymerization and/or lower average molecular weight than currently available hydrolyzed starches. Such characteristics make the hydrolyzed starch more easily digestible, and thus, more suitable for infant and/or elderly nutrition. For example, hydrolyzed starches described herein with higher DE values have lower molecular weights and are thus particularly suitable for infant and/or elderly nutrition.

EXAMPLES

Example 1: Analytical Methods

L*a*b* Hunter Color:

Thirty percent solutions were made of each composition by mixing stirring and heating to the point of boiling, stirring again and boiling a second time before adding back lost water. Aliquots of the solutions (18-19 g of solution) were placed on 2¼ inch petri dishes to obtain L*a*b* values. Samples were grouped by treatment type and by starting material composition. Hunter L*a*b* values were obtained by placing the petri dish on a large sampling port (2¼ inch diameter) and covered by an opaque cup. Clear samples were shown as dark (low L value) and opaque white samples were shown as white (high L* value).

Viscosity and Gel Strength Characterization:

The hydrolyzed starch samples were prepared by dispersing anywhere from 10% to 50% dry solids into cold deionized water, followed by heating and mixing to form a dispersion free of lumps. This hot solution was poured into the cup and bob viscometer which was equilibrated at 50° C.

Viscosity measurements were made using an Anton Paar MCR 502. Geometry used was cup and bob CC27. A shear rate of 200 1/s was used to monitor the sample as it was heated from 50° C. up to 95° C. No sample deformation was performed as the sample was cooled from 95° C. to 20° C. over the course of 38 min. When the sample cooled to 20° C. a shear rate scan from 0.1 1/s to 1000 1/s was run. The thermal profile of the scan started at 50° C. for 5 minutes and heated to 95° C. in a 23 minute interval and continued monitoring viscosity for 5 minutes at 95° C. The sample was cooled from 95° C. down to 20° C. over the course of 38 minutes and was held at 20° C. for 5 minutes prior to a shear rate scan starting at 0.1 1/s and proceeding to 1000 1/s over the course of 7 minutes.

The above aqueous preparations were used for gel strength measurements using a TAXT2 texture analyzer from Stable Micro Systems. The aqueous samples after viscosity measurements were refrigerated (~5° C.±2° C.) for 4 days in sealed container. After 4 days of storage, the samples were removed from the refrigerator and equilibrated to room temperature (22° C.). The gel strength measurements were performed at room temperature.

The instrument is equipped with a 5 Kg load cell, which is calibrated with a 2.5 Kg weight. Texture evaluation is done using the TAXT2 texture analyzer equipped with a stainless steel ½ inch diameter round nose finger probe. The parameters used are listed below:

Test Mode and Option: Measure Force in Compression;
Return to Start Parameters:
  Pre Test Speed: 4.00 mm/sec
  Test Speed: 2.00 mm/sec
  Post Test Speed: 4.00 mm/sec
  Rupture Test Dist.: 4.0 mm
  Distance: 10.0 mm
  Force: 100.0 g
  Time: 5.00 sec.
  Count: 5
  Load Cell: 5 Kg
  Temperature: 25° C.

Trigger:
Type: Auto
Force: 5.0 g

Essentially, the probe approaches the sample at 4 mm/sec until the surface is detected with a 5 g trigger force, then data acquisition starts. From the trigger point the probe continues at a reduced 2 mm/sec travelling 10 mm (1 cm) into the sample. The probe then reverses. The vial is held down to prevent the probe from lifting the vial when it returns to its starting position at 4 mm/sec.

The maximum resistance in grams of force is the value reported for gel strength.

Absolute Molecular Weight, DP Distribution, and Radius of Gyration:

Absolute molecular weight was characterized by size exclusion chromatography using an Alliance 2690 HPLC (high performance liquid chromatography) system, manufactured by Waters Corporation, Milford, Mass., coupled to a DAWN HELEOS II multi-angle light scattering (MALS) instrument, manufactured by Wyatt Technology, Santa Barbara, Calif., and a 2410 refractive index detector manufactured by Waters Corporation, Milford, Mass. Waters Corporation Styragel columns HR5 and HR4, connected in series, were used to separate the sample components. The column temperature was controlled at 60° C. and the sample compartment temperature was set to 40° C. The internal temperature of the refractive index detector was set to 40° C. The HPLC mobile phase, 50 mM lithium bromide in 90% dimethyl sulfoxide (DMSO) in water, flow rate was set to 0.4 mL/min and the total run time was 90 minutes. Waters Corporation Empower 3 software was used to control the Alliance 2690 HPLC and 2410 refractive index detector, and Wyatt Technology Astra 6.1 software was used to collect the light scattering and refractive index signals and perform the data analysis for calculating DP distribution and radius of gyration. Samples solutions were prepared by dispersing 200 mg of dried hydrolyzed starch product in mobile phase (50 mM lithium bromide in 90% DMSO in water). The solutions were uniformly dispersed by stirring for 1 hour at room temperature, boiling and stirring for 10 minutes, and then stirring overnight at room temperature. The final step was to filter the solutions, using a 1 um PTFE syringe filter disk, into a 2 mL HPLC vial.

Polydispersity:

Polydispersity is the ratio of weight average molecular weight (Mw) to number average molecular weight (Mn).

Example 2: Experimental Hydrolyzed Starch Prototypes

This pilot process included traditional starch liquefaction which utilized jet cooker and spray dryer equipment. The liquefaction variables, including enzyme dosage, pH, aqueous slurry temperature and liquefaction hold time, were adjusted to result in target dextrose equivalent, DE, in the final product. Experimental prototypes were made using DSM's alpha-amylase enzyme Maxamyl™ HT Ultra. The control thermostable liquid alpha amylase, GC100, which is produced from *Bacillus Licheniformis* and supplied by Danisco US Inc., and Liquozyme® SC DS, a thermostable alpha amylase supplied by Novozymes Inc, were used to make alternative prototypes that are compared to the experimental prototypes. Experimental hydrolyzed starch prototypes were made targeting DE of 1-2, 5, 10, and 18 for both native common and native waxy corn starch. Approximately 30 lbs was targeted for each prototype to undergo application and analytical testing. Due to capacity and throughput limits on the jet cooker, multiple trial runs were conducted to produce the full 30 lbs needed for each experimental DE. In all, eight sets of experimental prototypes were produced. The experimental prototypes produced with native common corn starch resulted in the following DE's: 0.81/0.63/0.80, 4.67/5.26, 9.04/10.80 and 19.1/16.3. These DE's matched satisfactorily with the target DE's of 1-2, 5, 10, and 18, respectively. Similarly, the experimental prototypes produced with native waxy corn starch resulted in the following DE's: 0.44/1.49, 8.40/8.05, 9.53/12.05, and 19.78/16.7. These DE's matched satisfactorily with the target DE's of 1-2, 5, 10, and 18, respectively.

In addition to the experimental prototypes, control prototypes were produced using GC100 α-amylase enzyme. Four control prototypes were produced targeting DE's of 1-2, 5, and 18. The control prototypes produced from native common corn starch resulted in the following DE's: 1.43/0.96, 5.55/5.26, and 19.2/18.0, which matched satisfactorily with the target DE's of 1-2, 5, and 18. The control prototype produced with native waxy corn starch resulted in DE's of 21.26/17.8, which matched satisfactorily with the target DE of 18. Commercial products and control prototypes made with the GC100 α-amylase were used as controls to compare to experimental prototypes.

Example 3: Process for Making Hydrolyzed Starch Prototypes

Materials: The starting base for the experimental prototypes included Cargill Gel 04230, Batch #01215CHYAA, a native waxy corn starch and Cargill Gel 03420, Batch #02415CHYBB, a native common corn starch. DSM's alpha-amylase enzyme Maxamyl™ HT Ultra was used to make the hydrolyzed starch prototypes and an α-amylase was used as a control enzyme. HCl (1:1) and NaOH (50% w/w concentration) were used.

Chemical Analysis: The moisture content of dried prototypes was determined using a gravimetric moisture meter. Dextrose Equivalent (DE) analysis was performed on both in-process liquid and final dried samples. The dried hydrolyzed starches of 1 DE and 5 DE values were tested for DE based on Schrool's titration method, which determines reducing sugars in the hydrolyzed starches by reaction with a stabilized alkaline solution of a copper salt. When reaction conditions (i.e., time, temperature, reagent concentration, and composition) are controlled, the amount of copper reduced is proportional to the amount of reducing sugars in the sample analyzed. In the current DE method, the reducing sugar concentration (expressed as dextrose) is estimated by iodometric determination of the unreduced copper remaining after reaction.

Schrool's titration method: Weigh 5.0 g (dry basis) of sample, place it in a 200 mL Kohlrausch flask, and dilute to volume with warm deionized water. Shake the flask to ensure the sample dispersion is free of clumps of dried hydrolyzed starch. Transfer the contents of the flask to a 250 mL beaker. Pipet 20.0 mL of the sample dispersion into a 250 mL Erlenmeyer flask and add 20.0 mL of freshly prepared Schoorl's solution (10 mL each of Fehling's Solution A and B, available from Sigma Aldrich). Add 10.0 mL of deionized water to the flask. Add glass beads to the flask to prevent bumping during the next steps of boiling. Cover the mouth of the flask. Prepare a blank containing 20.0 mL of Schoorl's Solution and 30.0 mL of deionized water. Place both flasks on a hot plate (400° C.) and bring to a boil in about three minutes. Continue boiling for two minutes and then cool quickly to room temperature using a 50° F. water bath or in the sink under cold running water. Add 10.0 mL of 30% KI solution and then add 10.0 mL of 30% H2SO4 solution. Titrate immediately with 0.1 N Na2S2O3 solution. Near the endpoint (appearance of a milky color), add starch indicator and titrate until the blue starch-iodine color is discharged.

Calculation of DE value: Subtract the sample titer from the blank titer. Find the Reducing Sugar content (Dextrose Equivalent) as below:

$$\% \text{ Reducing Sugar (dry basis)} = \frac{\text{mg Dextrose (from Table)} \times 200 \text{ mL} \times 100\%}{\text{Sample Wt. of 5 g (dry basis)} \times 20 \text{ mL} \times 1000}$$

$$= \frac{\text{mg Dextrose}}{\text{Sample Wt. (dry basis)}}$$

For the higher DE hydrolyzed starch powders, such as DE 10 and DE 18 samples, an FTIR (Fourier Transform Infrared Spectroscopy) method was used. The FTIR instrument analyzes by measuring the reflectance of a sample at a specific wavelength in the mid-infrared region of the electromagnetic spectrum. The instrument is calibrated using the samples of known DE prior to the tests.

Liquefaction Method: The liquefaction process consisted of jet cooking of aqueous starch slurry (concentration range from 12-30% dry solids in the presence of DSM's alpha-amylase enzyme Maxamyl™ HT Ultra, a starch hydrolyzing enzyme). To jet cook aqueous starch slurry, the slurry was pumped at a fixed rate through a direct injection steam heater. Direct steam injection generates high temperature (95° C.-130° C.) and shear that converts starch slurry into starch paste. Starch paste was then pumped through a flash chamber (reducing temperature instantaneously to about 90° C.), and then it is finally collected into a product tank equipped with a cover and an agitator.

The cooking temperature during jet cooking step was targeted between 110-120° C. After the jet cooking step, liquefied starch in the product tank was held at 90° C. until a desired degree of hydrolysis in liquefact is achieved. The product was then spray dried. Below is a step-wise procedure that was followed for this starch liquefaction process:

1. Starch slurry preparation: In a mixing tank (feed tank), prepare 25% (w/w starch solids) starch slurry in water using 10 Kg starch (commercial base). Add required quantity of water in the mixing tank first, and then turn on mixing at a slow speed. Slowly add the entire quantity of starch to the mixing tank while contents are mixed continuously at a slow speed. Maintain slurry at ambient temperature. Adjust speed of mixing to prevent settling of starch solids. Allow starch to hydrate for a minimum of 15 minutes.

2. pH adjustment & preparing for enzyme conversion: Check pH and the temperature of the slurry in feed tank. Adjust pH to 4.8-5.2 using 1:1 HCl acid buffer. Record quantity of acid buffer used. After pH adjustment, continue mixing of the slurry at a gentle speed. Weigh the required quantity of enzyme in a clean plastic container and add enzyme into the slurry. Five minutes after adding the enzyme, check the pH and the temperature of the slurry once again. Continue mixing.

3. Jet Cooking Step: Using water as the feed for the jet cooker to prepare jet cooker and equilibrate the cooking temperature between 110-117° C. and outlet temperature of 95° C. (atmospheric flash in product tank). Once the cooking conditions are set, start feeding the starch slurry into the jet cooker. Record this time as time 0 by starting a stop watch. Keep the stop watch running until the completion of step #3 and #4 to record total liquefaction time. Continue mixing of the slurry while the slurry is being pumped through jet cooker. Record the time that the liquefact starts to come out of the jet-cooker output; this is the residence time of liquefact in jet cooker piping. Collect liquefact into product tank equipped with overhead mixer and temperature control up to 95° C.

4. Holding Liquefact at 95° C.: Hold liquefact in product tank at 95° C. for a desired holding time that corresponds to a DE (extent of hydrolysis) value desired in final products. Continue mixing the liquefact at a slow speed. Total liquefaction times are recorded.

5. Enzyme Kill Step: Immediately after completion of desired holding times (step 4 above), adjust pH to 2.7-3.0 at 95° C. and hold for 15 minutes. Continue mixing the liquefact at a slow speed. To ensure complete inactivation of enzyme, temperature is controlled and holding time is 15 minutes.

6. Adjust pH between to 4.5±0.5. Continue mixing of liquefact. Adjust pH to 4.5±0.5 in liquefact using NaOH base buffer. Then, immediately draw a liquid sample for DE measurement. The starch liquefact is released for spray drying.

7. Cool and Dilute: Immediately after completion of pH adjustment, let the slurry cool down to 55-60° C. (use cooling water circulation if needed). If desired prototype is in the 1-2 DE range, heating is not turned off because low-DE products will thicken quickly and make further processing difficult. Before spray drying a product with a 1-2 DE range, dilute to approximately 15% DS, to allow the product to be transferred to spray dryer through peristaltic pump.

Spray Drying Method: A Niro spray dryer was used for drying the starch liquefact. Below is a step-wise procedure of spray drying that was followed in the current study.

1. Ensure liquefact prepared by jet cooker is stored in product tank at 50-65° C. while continuously stirring the contents at slow speed to prevent stratification.

2. Transfer approximately 10 to 15 L of hot liquefact (at 50-65° C.) from product tank to a 5 gallon white plastic pail. Immerse this plastic pail into a 60° C. water bath. Set an overhead mixer to continuously mix the contents in the pail at a slow speed. Record % solids in the liquefact using moisture meter. As needed, adjust % solids in liquefact to lower level using sanitized water to ensure optimum spray drying operation.

3. Feed deionized water into the spray dryer to equilibrate the inlet temperature of the dryer to approximately 200° C. and the outlet temperature to approximately 100° C.

4. Switch the feed from water to liquefaction. Monitor both the inlet and outlet temperatures.

5. Record feed rate, inlet and outlet temperatures of spray dryer. Collect~15 lbs of dried product, and store in air tight packaging. Record the final weight and % moisture of the dried product.

Example 4: Characteristics of Experimental Hydrolyzed Starch Prototypes

This process created eight experimental hydrolyzed starches and four control hydrolyzed starches. Table 1 lists the prototypes and their final dried weights. Table 2 lists the control prototypes and their final dried weights.

TABLE 1

| Starch Type | Target DE | Trial | Final DE | Amnt Dried Product (lbs) | Total Amnt (lbs) |
|---|---|---|---|---|---|
| Native Common | 1-2 DE | #1 | 0.81 | 11.60 | 42.60 |
| Native Common | | #2 | 0.63 | 14.80 | |
| Native Common | | #3 | 0.80 | 16.20 | |
| Native Common | 5 DE | #5 | 4.67 | 15.80 | 34.60 |
| Native Common | | #6 | 5.26 | 18.80 | |
| Native Common | 10 DE | #7 | 9.04 | 17.40 | 33.51 |
| Native Common | | #8 | 10.80 | 16.11 | |
| Native Common | 18 DE | #10 | 19.1 | 16.20 | 31.17 |
| Native Common | | #5 P-1 | 16.3 | 14.97 | |
| Native Waxy | 1-2 DE | #12 | 0.44 | 16.58 | 31.63 |
| Native Waxy | | #13 | 1.49 | 15.05 | |
| Native Waxy | 5 DE | #14 | 8.40 | 17.55 | 34.30 |
| Native Waxy | | #15 | 8.05 | 16.75 | |
| Native Waxy | 10 DE | #16 | 9.53 | 17.41 | 35.94 |
| Native Waxy | | #17 | 12.05 | 18.53 | |
| Native Waxy | 18 DE | #18 | 19.78 | 16.54 | 34.54 |
| Native Waxy | | #7 P-1 | 16.7 | 18.00 | |
| Pea Starch | 1 DE | #31 | 0.55 | 5.68 | 5.68 |

TABLE 2

| Starch Type | Enzyme | Target DE | Trial | Final DE | Dried Product (lbs) | Combined Total (lbs) |
|---|---|---|---|---|---|---|
| Native Waxy | GC100 | 18 DE | #20 | 21.65 | 15.98 | 34.36 |
| Native Waxy | GC100 | | #11 P-1 | 17.8 | 18.38 | |
| Native Common | GC100 | 5 DE | #24 | 5.55 | 16.89 | 34.07 |
| Native Common | GC100 | | #25 | 5.26 | 17.18 | |
| Native Common | GC100 | 18 DE | #26 | 19.2 | 15.28 | 33.25 |
| Native Common | GC100 | | #10 P-1 | 18.0 | 17.97 | |
| Native Common | GC100 | 1 DE | #28 | 1.43 | 14.52 | 31.46 |
| Native Common | GC100 | | #29 | 0.96 | 16.94 | |
| Pea Starch | GC 100 | 1 DE | #32 | 2.19 | 7.42 | 7.42 |
| Native Waxy | Liquozyme | 5 DE | #30 | 7.82 | 10.71 | 10.71 |
| Control Hydrolyzed starch samples that are commercial available from Cargill Manufacturing Plants | | | | | | |
| Cargill Dry 01909 (Native Common) | GC 100 | 10 DE | — | 11.4 | — | — |
| Cargill Dry 01960 (Waxy corn starch) | GC 100 | 10 DE | — | 11.80 | — | — |
| Cargill Dry 01901 (Waxy corn starch) | GC 100 | 1-2 DE | — | 1.5 | — | — |
| Cargill Dry 01956 (Waxy corn starch) | GC 100 | 5 DE | — | 8.2 | — | — |

Results: 1 DE Waxy Starch-Based Hydrolyzed Starch

Table 3 and 4 demonstrate the analytical properties of 1 DE waxy starch-based hydrolyzed starches discussed above.

Tables 3 and 4 show the properties of 1 DE experimental hydrolyzed starch made using the alpha amylase derived from *Pseudomonas fluorescens* Biovar I and 1DE control hydrolyzed starch made using GC100 alpha amylase.

1 DE experimental hydrolyzed starch formed milky white dispersions compared to clear, transparent dispersions formed by control hydrolyzed starch. 1 DE experimental hydrolyzed starch showed lower average molecular weight (386 KDa) vs control hydrolyzed starch made using GC100 (709 KDa). 1 DE experimental hydrolyzed starch showed gelling at 30% solids in aqueous medium vs control hydrolyzed starch made using GC100, which showed no gel formation. 1 DE experimental hydrolyzed starch also showed gelling at 20% solids in aqueous medium. 1 DE experimental hydrolyzed starch showed lower viscosity as a function of temperature and shear compared to control hydrolyzed starch made using GC100. The lower in-use process viscosity enables easier and more efficient in-process handling, dispensing and pumping. In some aspects, this may also enable higher solids handling at higher temperature/shear conditions compared to control hydrolyzed starch.

TABLE 3

| | Average M. Wt (Da) | | 1 DE Waxy hydrolyzed starch | | |
|---|---|---|---|---|---|
| | | | EXP #13 | Exp# 12 | CTRL 1901 (Cargill Dry 01901) |
| DP range | From | to | (1.49 DE) | (0.44 DE) | (1.5 DE) |
| DP 1-5 | 0 | 909 | 0 | 0 | 0 |
| DP 6-9 | 909 | 1,557 | 0 | 0 | 0 |
| DP 10-19 | 1,557 | 3,177 | 0 | 0 | 0 |
| DP 20-45 | 3,177 | 7,389 | 0 | 0 | 2.29 |
| DP 46-125 | 7,389 | 20,349 | 15.97 | 0 | 7.79 |
| DP 126-280 | 20,349 | 45,459 | 15.47 | 0 | 9.68 |
| DP 281-600 | 45,459 | 97,299 | 14.58 | 0 | 12.02 |
| DP 601-1500 | 97,299 | 243,828 | 18.56 | 0 | 16.11 |
| DP 1500-3075 | 243,828 | 500,000 | 14.31 | 30.14 | 15.03 |

TABLE 3-continued

| | 1 DE Waxy hydrolyzed starch | | | |
|---|---|---|---|---|
| | Average M. Wt (Da) | | EXP #13 | Exp# 12 | CTRL 1901 (Cargill Dry 01901) |
| DP range | From | to | (1.49 DE) | (0.44 DE) | (1.5 DE) |
| DP 3075-6172 | 500,000 | 1,000,000 | 11.25 | 18.54 | 14.59 |
| DP 6172-7716 | 1,000,000 | 1,250,000 | 2.55 | 5.06 | 4.2 |
| DP 7716-9259 | 1,250,000 | 1,500,000 | 1.69 | 4.09 | 3.2 |
| DP 9259-10802 | 1,500,000 | 1,750,000 | 1.25 | 3.46 | 2.5 |
| DP 10802-12346 | 1,750,000 | 2,000,000 | 0.86 | 2.97 | 2.09 |
| DP 12346-15432 | 2,000,000 | 2,500,000 | 1.07 | 4.89 | 3.05 |
| DP 15342-18518 | 2,500,000 | 3,000,000 | 0.62 | 3.93 | 2.13 |
| > DP 18518 | >3,000,000 | | 1.82 | 26.92 | 5.34 |
| DE | | | 1.49 | 0.44 | 1.5 |
| Polydispersity | | | 7 | 3 | 12 |
| (Rz, nm) | | | 26 | 47 | 24 |
| Average M.Wt (Kda) | | | 386 | 2464 | 709 |

TABLE 4

| | EXP #13 (1.49 DE) | EXP # 12 (0.44 DE) | CTRL (1901) (1.5 DE) |
|---|---|---|---|
| Gel Formation @ 30% | YES | — | NO |
| Gel Strength (g) (30% solids) | 1000 | — | 0 |
| Gel Strength (g) (50% solids) | Not tested | — | Not tested |
| Viscosity (cp) at 95 C. at 200 s$^{-1}$ | 16.7 | 89.45 | 26.8 |
| Viscosity (cp) at 50 C. at 200 s$^{-1}$ | 54.7 | 326.9 | 91.3 |
| Viscosity (cp) at 20 C. at 1000 s$^{-1}$ | 199 | 960.9 | 340 |
| Viscosity (cp) at 20 C. at 100 s$^{-1}$ | 209 | 1346 | 365 |
| Clarity (Scores) | Opaque | Opaque | Transparent |
| L*a*b* Hunter Color | L* 89.38 a* −1.31 b* 4.52 | — | L* 11.41 a* −0.86 b* −5.1 |

Results: 5 DE Waxy Starch-Based Hydrolyzed Starch

Tables 5, 6, and 7 demonstrate the analytical properties of 5 DE waxy starch-based hydrolyzed starches discussed above. Tables 6 and 7 show the properties of 5 DE experimental hydrolyzed starch made using the alpha amylase derived from *Pseudomonas fluorescens* Biovar I and 5 DE control hydrolyzed starch made using GC100 alpha amylase. Table 5 shows the properties of the 5 DE experimental hydrolyzed starch made using the alpha amylase derived from *Pseudomonas fluorescens* Biovar I and the 5 DE control hydrolyzed starch made using Liquozyme® alpha amylase.

5 DE experimental hydrolyzed starch formed milky white dispersion compared to clear/transparent dispersion formed by control hydrolyzed starch (CNTRL 1956) made using GC100 alpha amylase. 5 DE experimental hydrolyzed starch demonstrated lower average molecular weight (35 KDa or 17 kDa) vs control hydrolyzed starch made using GC100 alpha amylase (75 KDa) or control hydrolyzed starch made using Liquozyme® (85 KDa). % DE experimental hydrolyzed starch showed gelling at 30% solids in aqueous medium versus control hydrolyzed starch made using GC100 alpha amylase, which showed no gel formation. 5 DE experimental hydrolyzed starch showed lower viscosity as a function of temperature and shear compared to control hydrolyzed starch made using GC100 alpha amylase, and 5 DE experimental hydrolyzed starch showed a different oligosaccharide composition compared to Control hydrolyzed starch.

TABLE 5

| | 5 DE WAXY HYDROLYZED STARCH % Abundance | |
|---|---|---|
| DP range | EXP # 14 (8.40 DE) | Liquozyme EXP # 30 (7.82 DE) |
| 1-5 | 0 | 0 |
| 6-9 | 0 | 0 |
| 10-19 | 34.93 | 27.49 |
| 20-45 | 33.05 | 7.59 |
| 46-125 | 17.79 | 14.35 |
| 126-280 | 5.62 | 15.83 |
| 281-600 | 3.18 | 12.96 |
| 601-1500 | 2.36 | 12.07 |
| >1500 | 3.07 | 9.71 |
| DE | 8.4 | 7.82 |
| Polydispersity (Mw/Mn) | 9 | 14 |
| Radius of Gyration (Rz, nm) | 18 | 11 |
| Av M.Wt (Kda) | 35 | 84 |

TABLE 6

| | 5 DE WAXY HYDROLYZED STARCH % Abundance | | |
|---|---|---|---|
| DP range | EXP # 14 (8.40 DE) | EXP# 15 (8.05 DE) | CTRL 1956 (Cargill Dry 01956) (8.2 DE) |
| 1-5 | 0 | 0.95 | 0 |
| 6-9 | 0 | 4.03 | 10.84 |
| 10-19 | 34.93 | 34.69 | 18.63 |
| 20-45 | 33.05 | 31.85 | 6.43 |
| 46-125 | 17.79 | 17.67 | 11.31 |
| 126-280 | 5.62 | 6 | 16.27 |
| 281-600 | 3.18 | 2.95 | 14.15 |
| 601-1500 | 2.36 | 1.4 | 13.53 |
| >1500 | 3.07 | 0.47 | 8.84 |
| DE | 8.4 | 8.05 | 8.2 |
| Polydispersity (Mw/Mn) | 9 | 5 | 16 |
| Radius of Gyration (Rz, nm) | 18 | 15 | <10 |
| Av M.Wt (Kda) | 35 | 17 | 75 |

TABLE 7

|  | EXP # 14 (DE 8.40) | EXP # 15 (DE 8.05) | Liquozyme EXP # 30 (7.82 DE) | CTRL 1956 (DE 8.2) |
|---|---|---|---|---|
| Gel Formation | Yes | — | Yes | N |
| Gel Strength (g) (30% solids) | 3 | — | 0 | 0 |
| Gel Strength (g) (40% solids) | 179 | — | 10 | 0 |
| Gel Strength (g) (50% solids) | 1689 | — | 200 | 1724 |
| Viscosity (cp) at 95 C. at 200 $s^{-1}$ | 2.8 | 2.35 | — | 4.8 |
| Viscosity (cp) at 50 C. at 200 $s^{-1}$ | 6.8 | 5.37 | Not tested | 12.3 |
| Viscosity (cp) at 20 C. at 1000 $s^{-1}$ | 16.4 | 12.54 | Not tested | 36.6 |
| Viscosity (cp) at 20 C. at 100 $s^{-1}$ | 18.2 | 13.53 | Not tested | 34.4 |
| Clarity (Scores) | Opaque | Opaque | Opaque | Transparent |
| L*a*b* Hunter Color | L* 77.39 a* −1.51 b* 9.73 | — | Not tested | L* 3.16 a* −0.01 b* −0.58 |

Results: 10 DE Waxy Starch-Based Hydrolyzed Starch

Tables 8 and 9 demonstrate the analytical properties of 10 DE waxy starch-based hydrolyzed starches discussed above. Specifically, Tables 8 and 9 shows the properties of 10 DE experimental hydrolyzed starch made using the alpha amylase derived from Pseudomonas fluorescens Biovar I and 10DE control hydrolyzed starch made using GC100 alpha amylase.

10 DE experimental hydrolyzed starch formed milky white dispersions compared to clear, transparent dispersions formed by control hydrolyzed starch. 10 DE experimental hydrolyzed starch showed lower average molecular weight (11 kDa and 7 kDa) vs control hydrolyzed starch (44 KDa). 10 DE experimental hydrolyzed starch showed gelling at 30% solids in aqueous medium vs control hydrolyzed starch, which showed no gel formation. 10 DE experimental hydrolyzed starch showed lower viscosity as a function of temperature and shear compared to the control hydrolyzed starch.

10 DE experimental hydrolyzed starch showed different oligosaccharide composition compared to the control hydrolyzed starch made using GC100 alpha amylase. 10 DE experimental hydrolyzed starch contained only about 1% (by wt) oligosaccharide fractions that are higher than DP 601 whereas the control hydrolyzed starch made using GC100 alpha amylase contained >13% by wt of oligosaccharide compositions that are higher than DP 601. In some aspects, the 10 DE experimental hydrolyzed starch may be useful for infant or elderly nutrition where low molecular weight hydrolyzed starches are desired.

TABLE 8

10 DE WAXY HYDROLYZED STARCH
% Abundance

| DP range | EXP # 16 (9.53 DE) | EXP #17 (12.05 DE) | CTRL 1960 (Cargill Dry 01960) (11.8 DE) |
|---|---|---|---|
| 1-5 | 0 | 0 | 9.81 |
| 6-9 | 7.26 | 4.53 | 17.83 |
| 10-19 | 31.16 | 53.46 | 12.85 |
| 20-45 | 34.78 | 29.74 | 6.51 |
| 46-125 | 18.67 | 8.35 | 12.43 |
| 126-280 | 4.96 | 1.78 | 16.33 |
| 281-600 | 2.14 | 0.95 | 11.87 |
| 601-1500 | 0.77 | 1.19 | 8.84 |
| >1500 | 0.26 | 0 | 3.53 |
| DE | 9.5 | 12.05 | 11.8 |
| Polydispersity (Mw/Mn) | 3 | 3 | 17 |
| Radius of Gyration (Rz, nm) | 12 | <10 | <10 |
| Av M.Wt (Kda) | 11 | 7 | 44 |

TABLE 9

|  | EXP #16 (9.53 DE) | EXP # 17 (12.05 DE) | CTRL (1960) (11.8 DE) |
|---|---|---|---|
| Gel Formation | Yes | — | NO |
| Gel Strength (g) (30% solids) | 7 | — | 0 |
| Gel Strength (g) (50% solids) | 362 | — | 0 |
| Viscosity (cp) at 95 C. at 200 $s^{-1}$ | 2.4 | 2.29 | 3.5 |
| Viscosity (cp) at 50 C. at 200 $s^{-1}$ | 5.6 | 4.39 | 8.5 |
| Viscosity (cp) at 20 C. at 1000 $s^{-1}$ | 15.4 | 11.66 | 23.9 |
| Viscosity (cp) at 20 C. at 100 $s^{-1}$ | 13.4 | 10.1 | 21.8 |
| Clarity (Scores) | Opaque | — | Transparent |
| L*a*b* Hunter Color | L* 71.25 a* −1.23 b* 8.09 | — | L* 3.26 a* −0.11 b* −0.71 |

Results: 18 DE Waxy Starch-Based Hydrolyzed Starch

Tables 10 and 11 demonstrate the analytical properties of 18 DE waxy starch-based hydrolyzed starches discussed above. Specifically, Tables 10 and 11 shows the properties of 18 DE experimental hydrolyzed starch made using the alpha amylase derived from Pseudomonas fluorescens Biovar I and 18DE control hydrolyzed starch made using GC100 alpha amylase.

18 DE experimental hydrolyzed starch formed milky white dispersions compared to clear, transparent dispersions formed by control hydrolyzed starch made using GC100. 18 DE experimental hydrolyzed starch showed lower average molecular weight (4 Da) vs control hydrolyzed starch made using GC100 (16 KDa). 18 DE experimental hydrolyzed starch had a different oligosaccharide composition compared to control hydrolyzed starch. 18 DE experimental hydrolyzed starch contained less than 1% (by wt) oligosaccharide fractions that are higher than DP 601, whereas the control hydrolyzed starch made using GC100 contained >4% by wt of oligosaccharide compositions that are higher than DP 601. In some aspects, the 18 DE experimental hydrolyzed starch may be useful for infant or elderly nutrition where low molecular weight hydrolyzed starches are desired.

TABLE 10

18 DE WAXY HYDROLYZED STARCH
% Abundance

| DP range | EXP # 18 (19.78 DE) | #7 (Phase I) (16.7 DE) | CTRL GC 100 (Phase I - #11) (17.8 DE) |
|---|---|---|---|
| 1-5 | 15.01 | 7.81 | 19.58 |
| 6-9 | 19.24 | 24.22 | 33.22 |
| 10-19 | 43.97 | 41.65 | 5.82 |
| 20-45 | 18.79 | 20.34 | 6.93 |
| 46-125 | 1.79 | 4.05 | 14.74 |
| 126-280 | 0.71 | 0.7 | 12.3 |
| 281-600 | 0.48 | 0.32 | 5.29 |
| 601-1500 | 0 | 0.91 | 1.54 |
| >1500 | 0 | 0 | 0.57 |
| DE | 19.7 | 16.7 | 18 |
| Polydispersity (Mw/Mn) | 2 | 3 | 13 |
| Radius of Gyration (Rz, nm) | <10 | <10 | 17 |
| Av M.Wt (Kda) | 4 | 4 | 16 |

TABLE 11

| | EXP # 18 (19.78 DE) | EXP # 7 P-1 (16.7 DE) | CTRL GC 100 (17.8 DE) |
|---|---|---|---|
| Gel Formation | NO | — | NO |
| Gel Strength (g) (30% solids) | 0 | — | 0 |
| Gel Strength (g) (50% solids) | 0 | — | 0 |
| Viscosity (cp) at 95 C. at 200 s$^{-1}$ | 2.06 | 2.16 | 2.16 |

TABLE 11-continued

| | EXP # 18 (19.78 DE) | EXP # 7 P-1 (16.7 DE) | CTRL GC 100 (17.8 DE) |
|---|---|---|---|
| Viscosity (cp) at 50 C. at 200 s$^{-1}$ | 3.35 | 3.76 | 3.67 |
| Viscosity (cp) at 20 C. at 1000 s$^{-1}$ | 11.3 | 11.53 | 11.3 |
| Viscosity (cp) at 20 C. at 100 s$^{-1}$ | 7.15 | 8.22 | 7.7 |
| Clarity (Scores) | Clear | Clear | Clear |
| L*a*b* Hunter Color | L* 27.65 a* −1.38 b* −2.1 | | L* 25.39 a* −1.36 b* −1.24 |

Results: 1 DE Common Starch-Based Hydrolyzed Starch

Tables 12 and 13 demonstrate the analytical properties of 1 DE common starch-based hydrolyzed starches discussed above.

1 DE experimental hydrolyzed starch showed lower average molecular weight (2835 KDa and 2108 kDa) vs control hydrolyzed starch (4078 KDa). Despite the lower average molecular weight, the experimental hydrolyzed starch formed gels with similar strength and showed higher viscosity as a function of shear and temperatures compared to the control. 1 DE experimental hydrolyzed starch showed higher viscosities at 25 to 95° C., demonstrating higher shear and temperature tolerance compared to the control hydrolyzed starch.

TABLE 12

| | Average M. Wt (Da) | | 1 DE common hydrolyzed starch | | |
|---|---|---|---|---|---|
| DP range | From | to | EXP #1 (0.81 DE) | EXP # 2 (0.63 DE) | Control # 29 (0.96 DE) |
| DP 1-5 | 0 | 909 | 0 | 0 | 0 |
| DP 6-9 | 909 | 1,557 | 0 | 0 | 0 |
| DP 10-19 | 1,557 | 3,177 | 0 | 0 | 0 |
| DP 20-45 | 3,177 | 7,389 | 0 | 0 | 0 |
| DP 46-125 | 7,389 | 20,349 | 0 | 0 | 0 |
| DP 126-280 | 20,349 | 45,459 | 0 | 0 | 0 |
| DP 281-600 | 45,459 | 97,299 | 0 | 0 | 0 |
| DP 601-1500 | 97,299 | 243,828 | 24.3 | 0 | 0 |
| DP 1500-3075 | 243,828 | 500,000 | 21.16 | 29.95 | 0 |
| DP 3075-6172 | 500,000 | 1,000,000 | 11.93 | 17.54 | 29.06 |
| DP 6172-7716 | 1,000,000 | 1,250,000 | 3.38 | 5.56 | 5.54 |
| DP 7716-9259 | 1,250,000 | 1,500,000 | 2.75 | 3.48 | 5.68 |
| DP 9259-10802 | 1,500,000 | 1,750,000 | 2.4 | 2.81 | 5.89 |
| DP 10802-12346 | 1,750,000 | 2,000,000 | 2.06 | 2.43 | 3.48 |
| DP 12346-15432 | 2,000,000 | 2,500,000 | 3.6 | 4.08 | 4.81 |
| DP 15342-18518 | 2,500,000 | 3,000,000 | 2.99 | 3.34 | 3.96 |
| >DP 18518 | >3,000,000 | | 25.44 | 30.82 | 41.57 |
| DE | | | 0.6 | 0.81 | 0.96 |
| Polydispersity | | | 4 | 5 | 3 |
| (Rz, nm) | | | 53 | 43 | 62 |
| Average M.Wt (Kda) | | | 2835 | 2108 | 4078 |

TABLE 13

1 DE COMMON HYDROLYZED STARCH

| | EXP #2 (0.81 DE) | EXP# 1 (0.63 DE) | CTRL #29 (0.96 DE) |
|---|---|---|---|
| Gel Formation | YES | — | YES |
| Gel Strength (g) (30% solids) | 2600 | — | 2700 |

TABLE 13-continued

| | 1 DE COMMON HYDROLYZED STARCH | | |
|---|---|---|---|
| | EXP #2 (0.81 DE) | EXP# 1 (0.63 DE) | CTRL #29 (0.96 DE) |
| Gel Strength (g) (50% solids) | Not measured | — | Not measured |
| Viscosity (cp) at 95 C. at 200 s$^{-1}$ | 1629 | 1657 | 797 |
| Viscosity (cp) at 50 C. at 200 s$^{-1}$ | 6780 | 6584 | 2710 |
| Viscosity (cp) at 20 C. at 1000 s$^{-1}$ | 2350 | 2509 | 753 |
| Viscosity (cp) at 20 C. at 100 s$^{-1}$ | 8510 | 9084 | 1210 |
| Clarity (Scores) | Opaque | Opaque | Opaque |
| L*a*b* Hunter Color | L* 88.07 a* −2.68 b* 5.43 | — | L* 88.33 a* −2.31 b* 5.84 |

Results: 5 DE Common Starch-Based Hydrolyzed Starch

Tables 14 and 15 demonstrate the analytical properties of 5 DE common starch-based hydrolyzed starches discussed above.

5 DE experimental hydrolyzed starch showed lower average molecular weight (117 KDa and 56 kDa) vs control (592 KDa). Despite the lower average molecular weight, the 5 DE experimental hydrolyzed starch formed gels that showed stronger strength than that of control hydrolyzed starch gels. 5 DE experimental hydrolyzed starch demonstrated lower viscosities than that of control hydrolyzed starch samples when measured at a range of temperatures (20° C. to 95° C.) and shear rates (100 s$^{-1}$ t 100 s$^{-1}$).

TABLE 14

| | 5 DE COMMON HYDROLYZED STARCH % Abundance | | |
|---|---|---|---|
| DP range | EXP #5 (4.67 DE) | EXP #6 (5.26 DE) | CTRL #25 (5.26 DE) |
| 1-5 | 0 | 0 | 0 |
| 6-9 | 0 | 0 | 0 |
| 10-19 | 0 | 16.74 | 0 |
| 20-45 | 32.15 | 27.19 | 0 |
| 46-125 | 31.22 | 25.00 | 7.49 |
| 126-280 | 12.94 | 11.75 | 20.23 |
| 281-600 | 9.89 | 9.01 | 26.33 |
| 601-1500 | 7.81 | 6.94 | 15.65 |
| >1500 | 5.99 | 3.37 | 30.3 |
| DE | 4.67 | 5.26 | 5.3 |
| Polydispersity (Rz, nm) | 11 | 8 | 10 |
| | 32 | 24 | 39 |
| Average M. Wt (Kda) | 117 | 56 | 592 |

TABLE 15

| | EXP #5 (4.67 DE) | EXP #6 (5.26 DE) | CTRL #25 (5.55 DE) |
|---|---|---|---|
| Gel Formation | YES | — | YES |
| Gel Strength (g) (30% solids) | 400 | — | 160 |
| Gel Strength (g) (50% solids) | Not measured | — | Not measured |
| Viscosity (cp) at 95 C. at 200 s$^{-1}$ | 9 | 7.39 | 16.8 |
| Viscosity (cp) at 50 C. at 200 s$^{-1}$ | 27.7 | 20.67 | 58.7 |
| Viscosity (cp) at 20 C. at 1000 s$^{-1}$ | 72 | 56.26 | 147 |
| Viscosity (cp) at 20 C. at 100 s$^{-1}$ | 165 | 109.16 | 201 |
| Clarity (Scores) | Opaque | Opaque | Opaque |
| L*a*b* Hunter Color | L* 94.2 a* −1.45 b* 6.36 | — | L* 88.82 a* −2.82 b* 5.75 |

Results: 10 DE Common Starch-Based Hydrolyzed Starch

Tables 16 and 17 demonstrate the analytical properties of 10 DE common starch-based hydrolyzed starches discussed above.

10 DE experimental hydrolyzed starch showed lower average molecular weight (12 KDa and 18 kDa) vs control hydrolyzed starch (59 KDa). Despite the lower average molecular weight, 10 DE experimental hydrolyzed starch formed soft gels compared to no gel formation by the control hydrolyzed starch samples. 10 DE experimental hydrolyzed starch demonstrated lower viscosities than that of control hydrolyzed starch samples when measured at a range of temperatures (20° C. to 95° C.) and shear rates (100 s$^{-1}$ to 100 s$^{-1}$). 10 DE experimental hydrolyzed starch formed opaque, milky white dispersions compared to the clear dispersions formed by the control hydrolyzed starch samples.

TABLE 16

| | 10 DE COMMON HYDROLYZED STARCH % Abundance | | |
|---|---|---|---|
| DP range | EXP # 8 (10.80 DE) | EXP #7 (9.04 DE) | CTRL 1909 (Cargill Dry 01909) (11.4 DE) |
| 1-5 | 5.27 | 0 | 10 |
| 6-9 | 7.24 | 3.73 | 13.13 |
| 10-19 | 32.97 | 39.69 | 17.95 |
| 20-45 | 31.79 | 29.14 | 6.55 |
| 46-125 | 14.37 | 15.29 | 9.26 |
| 126-280 | 4.4 | 6.08 | 13.66 |
| 281-600 | 2.35 | 3.31 | 11.76 |
| 601-1500 | 1.02 | 1.76 | 11.07 |
| >1500 | 0.58 | 1.01 | 6.61 |
| DE | 10.8 | 9.04 | 11.4 |
| Polydispersity (Rz, nm) | 4 | 5 | 23 |
| | 19 | 21 | <10 |
| Average M. Wt (Kda) | 12 | 18 | 59 |

TABLE 17

| | 10 DE COMMON HYDROLYZED STARCH | | |
|---|---|---|---|
| | EXP # 8 (10.80 DE) | EXP # 7 (9.04 DE) | CTRL 1909 (Cargill Dry 01909) (11.4 DE) |
| Gel Formation | YES | — | NO |
| Gel Strength (g) (30% solids) | 39 | — | 0 |
| Gel Strength (g) (50% solids) | — | — | — |
| Viscosity (cp) at 95 C. at 200 s$^{-1}$ | 3.3 | 5.09 | 3.7 |
| Viscosity (cp) at 50 C. at 200 s$^{-1}$ | 8.4 | 11.18 | 9.2 |
| Viscosity (cp) at 20 C. at 1000 s$^{-1}$ | 20.1 | 27.24 | 26.6 |
| Viscosity (cp) at 20 C. at 100 s$^{-1}$ | 28.8 | 49.44 | 23.8 |
| Clarity | Opaque | Opaque | Clear |
| L*a*b* Hunter Color | L* 90.75 a* −1.32 b* 7.21 | — | L* 3.2 a* −0.06 b* −0.65 |

Results: 18 DE Common Starch-Based Hydrolyzed Starch

Tables 18 and 19 demonstrate the analytical properties of 18 DE common starch-based hydrolyzed starch discussed above.

18 DE experimental hydrolyzed starch showed lower average molecular weight (7 KDa and 5 kDa) vs control hydrolyzed starch (26 KDa). 18 DE experimental hydrolyzed starch demonstrated a slightly higher viscosity compared to that of control hydrolyzed starch samples. This shows a lesser shear thinning as a functional of shear rate and temperature compared to that of hydrolyzed starch control. 18 DE experimental hydrolyzed starch formed opaque, milky white dispersions compared to the clear dispersions formed by the control hydrolyzed starch samples.

TABLE 18

18 DE COMMON HYDROLYZED STARCH % Abundance

| DP range | EXP #10 (19.1 DE) | #5 P-1 (16.3 DE) | #10 P-1 (18.0 DE) |
|---|---|---|---|
| 1-5 | 20.35 | 0 | 19.03 |
| 6-9 | 24.83 | 9.59 | 36.57 |
| 10-19 | 37.44 | 65.51 | 9.29 |
| 20-45 | 10.68 | 17.73 | 6.22 |
| 46-125 | 1.45 | 3.88 | 11.09 |
| 126-280 | 1.92 | 1.28 | 9.92 |
| 281-600 | 2.21 | 1.61 | 4.56 |
| 601-1500 | 0.75 | 0.39 | 1.96 |
| >1500 | 0.37 | 0 | 1.36 |
| DE | 19.1 | 16.3 | 18.0 |
| Polydispersity | 6 | 2 | 16 |
| (Rz, nm) | 13 | 20 | 39 |
| Average M. Wt (Kda) | 7 | 5 | 26 |

TABLE 19

| | EXP #10 (19.1 DE) | EXP # 5 P-1 (16.3 DE) | #10 P-1 (18.0 DE) |
|---|---|---|---|
| Gel Formation | NO | — | NO |
| Gel Strength (g) (30% solids) | 0 | — | 0 |
| Gel Strength (g) (50% solids) | Not measured | — | Not measured |
| Viscosity (cp) at 95 C. at 200 s$^{-1}$ | 3.2 | 2.35 | 2.3 |
| Viscosity (cp) at 50 C. at 200 s$^{-1}$ | 6.6 | 5.38 | 4.5 |
| Viscosity (cp) at 20 C. at 1000 s$^{-1}$ | 12.9 | 11.66 | 11.6 |
| Viscosity (cp) at 20 C. at 100 s$^{-1}$ | 19.2 | 10.1 | 10.7 |
| Clarity | Opaque | Opaque | Clear |
| L*a*b* Hunter Color | L* 70.32 a* −3.06 b* 5.15 | — | L* 34.97 a* −2.43 b* −0.43 |

Results: 1 DE Pea Starch-Based Hydrolyzed Starch

Tables 20 and 21 demonstrate the analytical properties of low DE Pea starch based hydrolyzed starches, targeting DE of 0 to 3. Table 22 shows EXP #31 Pea hydrolyzed starch forming stronger gel (as suggested by "too stiff to measure") compared to both Exp #2, a Maxamyl® HT Ultra based hydrolyzed starch and Exp #29, a control GC 100 based hydrolyzed starch (referred earlier in Table 13). A stronger gel formation suggests that the pea starch-derived hydrolyzed starch has a different composition than the common corn starch after treatment with Maxamyl® HT Ultra. The stronger gel formation may allow cost savings because less product would be needed to obtain similar thickening or gelling textures. Such pea starch-based maltodextrins may also have potential to function as novel binder and texturing for use in bakery for retaining moisture and in confectionary-soft candies and gummies for gelatin replacement and shape retention.

TABLE 20

Pea Hydrolyzed starch 1-2 DE % Abundance

| DP range | EXP #31 (0.55 DE) | EXP # 32 (GC100) (2.19 DE) |
|---|---|---|
| 1-5 | 0 | 0 |
| 6-9 | 0 | 0 |
| 10-19 | 0 | 0 |
| 20-45 | 0 | 3.22 |
| 46-125 | 0 | 30.46 |
| 126-280 | 0 | 10.99 |
| 281-600 | 27.14 | 6.81 |
| 601-1500 | 20.43 | 9.2 |
| >1500 | 52.43 | 39.31 |
| DE | 0.55 | 2.19 |
| Polydispersity (Mw/Mn) | 9 | 26 |
| Radius of Gyration (Rz, nm) | 39 | 31 |
| Av M. Wt (Kda) | 1607 | 714 |

TABLE 21

0-3 DE Pea Hydrolyzed starch

| | EXP #31 (0.55 DE) | EXP # 32 (GC100) (2.19 DE) |
|---|---|---|
| Gel Formation | YES | YES |
| Gel Strength (g) (30% solids) | — | — |
| Gel Strength (g) (50% solids) | — | — |
| Viscosity (cp) at 95 C. at 200 s$^{-1}$ | TOO STIFF of a PASTE to measure viscosity at 30% d.s. | 957 |
| Viscosity (cp) at 50 C. at 200 s$^{-1}$ | | 3580 |
| Viscosity (cp) at 20 C. at 1000 s$^{-1}$ | | 3600 |
| Viscosity (cp) at 20 C. at 100 s$^{-1}$ | | 18400 |
| Clarity | Opaque | Opaque |
| L* of L*a*b* | — | — |

Example 5: Dairy Applications_of Experimental Hydrolyzed Starch Prototypes

A. Sour Cream Application Testing

The formulations used for making full fat (15% fat) and light fat (9% fat) sour cream are listed Table 22 and 23, respectively. In full fat sour creams, a Cargill Texturizing Solution's functional stabilizer system, Vitex ASC 317, was used as base stabilizer. For light fat sour cream, Vitex ASC 208 was used as a stabilizer. For these trials, the current modified food starch present in the Vitex stabilizer systems was replaced 100% with the hydrolyzed starch as specified in the formulation Tables 22 and 23.

TABLE 22

Full Fat Sour Cream Formulation

| Ingredient | Control stabilizer (VITEX ASC 317) % | Experimental 1 DE Common Corn hydrolyzed starch (EXP# 1) % | Control 1 DE Common corn hydrolyzed starch (EXP# 28) % |
|---|---|---|---|
| Raw cream 36% B.F. | 45.60 | 45.60 | 45.60 |

TABLE 22-continued

Full Fat Sour Cream Formulation

| Ingredient | Control stabilizer (VITEX ASC 317) % | Experimental 1 DE Common Corn hydrolyzed starch (EXP# 1) % | Control 1 DE Common corn hydrolyzed starch (EXP# 28) % |
|---|---|---|---|
| Whole Milk | 49.98 | 49.98 | 49.98 |
| Non-fat dried milk | 2.00 | 2.00 | 2.00 |
| Whey Powder | 0.78 | 0.78 | 0.78 |
| Stabilizer (ASC 317) | 1.560 | 0.000 | 0.000 |
| Stabilizer (ASC 317-replace starch with EXP#1) | 0.000 | 1.560 | 0.000 |
| Stabilizer (ASC 317-replace starch with EXP#28) | 0.000 | 0.000 | 1.560 |
| Sodium Citrate | 0.050 | 0.050 | 0.050 |
| Potassium Sorbate | 0.030 | 0.030 | 0.030 |

TABLE 23

Light Sour Cream Formulation

| Ingredient | Control stabilizer (VITEX ASC 208) % | Experimental 1 DE Common Corn hydrolyzed starch (EXP# 1) % | Control 1 DE Common corn hydrolyzed starch (EXP# 28) % |
|---|---|---|---|
| Raw cream 36% B.F. | 18 | 18 | 18 |
| Whole Milk | 76.63 | 76.63 | 76.63 |
| Non-fat dried milk | 2.00 | 2.00 | 2.00 |
| Stabilizer (ASC 208) | 3.340 | 0.000 | 0.000 |
| Stabilizer (ASC 208-replace starch with EXP#1) | 0.000 | 3.340 | 0.000 |
| Stabilizer (ASC 208-replace starch with EXP#28) | 0.000 | 0.000 | 3.340 |
| Potassium Sorbate | 0.030 | 0.030 | 0.030 |

Manufacturing Method Used for Manufacturing Sour Cream (Same Process for Full Fat and Light)
1. Batch cold add all dry ingredients as listed in the formulation.
2. Preheat the batch vessel to 150° F.
3. Homogenize @ 2500 psi (2 stage)
4. Pasteurize (180° F. with 30 second hold)
5. Cool to 78° F.
6. Add culture Flay 672/overnight
7. Break at pH 4.6
8. Smooth (pump/screens)
9. Package and refrigerate Results Both the sour creams were manufactured with the intention of removing modified food starch from the product. The 1DE common-starch experimental hydrolyzed starch (EXP #1) was the most favorable product compared to the control hydrolyzed starch, EXP #28. The full fat and light fat sour creams made with the 1DE experimental hydrolyzed starch both maintained good viscosity, structure, and a smooth, shiny appearance, similar to the original sour cream formulations. The 1DE control hydrolyzed starch had weaker structure and lower viscosity. (Table 24).

TABLE 24

Viscosity comparison in control and experimental sour cream product

| | Control | Experimental 1 DE Common hydrolyzed starch (EXP#1) | Control 1 DE Common hydrolyzed starch (EXP# 28) |
|---|---|---|---|
| Full fat sour cream | | | |
| Viscosity at Day 1 (cps) | 154,000 | 119,000 | — |
| Viscosity Day 7 (cps) | 161,000 | 139,000 | 115,000 |
| Consistency | Good structure, smooth shiny appearance | Good structure, smooth shiny appearance | Weaker Structure |
| Light fat sour cream | | | |
| Viscosity at Day 1 (cps) | 107,000 | 132,000 | — |
| Viscosity Day 7 (cps) | 107,000 | 163,000 | 49,000 |
| Consistency | Good structure, smooth shiny appearance | Good structure, smooth shiny appearance | Weaker Structure |

B. Yogurt Application Testing

The formulations for gelatin replacement in regular (2% fat) yogurt are shown in Table 25. A Cargill Texturizing Solutions Functional System, Vitex AYS 79K, was used as the basis for the stabilizer with all trials. In these trials, the current gelatin was replaced with hydrolyzed starch to meet 4.43% of the total formulation and the weight of the functional system was adjusted accordingly.

TABLE 25

Yogurt formulation

| Ingredient | Control stabilizer (AYS 79K) % | Experimental 1 DE Common Corn hydrolyzed starch (EXP# 1) % | Control 1 DE Common corn hydrolyzed starch (EXP# 28) % | Experimental 1 DE Waxy Corn (EXP#5) % |
|---|---|---|---|---|
| Skim Milk | 57.7 | 57.7 | 57.7 | 57.7 |
| Whole Milk | 31.00 | 31.00 | 31.00 | 31.00 |
| Non-fat dried milk | 2.50 | 2.50 | 2.50 | 2.50 |
| Experimental hydrolyzed starch | 0.00 | 0.00 | 0.00 | 0.00 |
| Stabilizer (AYS 79 K) | 2.30 | 0.00 | 0.00 | 0.00 |

TABLE 25-continued

| | Yogurt formulation | | | |
|---|---|---|---|---|
| Ingredient | Control stabilizer (AYS 79K) % | Experimental 1 DE Common Corn hydrolyzed starch (EXP# 1) % | Control 1 DE Common corn hydrolyzed starch (EXP# 28) % | Experimental 1 DE Waxy Corn (EXP#5) % |
| Stabilizer (AYS 79K-replace starch with EXP#1) | 0.000 | 2.30 | 0.000 | 0.000 |
| Stabilizer (AYS 79K-replace starch with EXP#5) | 0.000 | 0.000 | 0.000 | 2.3 |
| Stabilizer (AYS 79K-replace starch with EXP#28) | 0.000 | 0.000 | 2.30 | 0.000 |
| Sugar | 6.50 | 6.50 | 6.50 | 6.50 |
| Potassium Sorbate | 0.030 | 0.030 | 0.030 | 0.030 |

Manufacturing Method Used to Make Yogurt:
1. Add non-fat dry milk, whey protein concentrate to milk phase (use defoamer). Hydrate 10 minutes
2. Add dry ingredients. Hydrate 10 minutes
3. Preheat to 190° F.
4. Homogenize 1000 psi (500 $1^{st}$/500 $2^{nd}$) 2 stage
5. Cool to 105-108° F.
6. Collect into stainless container
7. Add culture/Break at pH 4.65-4.70
8. Pump through cooling press to 55-60° F.
9. Use hand mixer on speed setting High for 90 seconds
10. Refrigerate and evaluate after 24 hours.

Results:

Yogurt was manufactured to replace gelatin with experimental hydrolyzed starch in the product. The removal of gelatin expands yogurt into a vegetarian option. The experimental hydrolyzed starch, EXP #1 showed acceptable results of texture and body in the yogurt, compared to the control hydrolyzed starch, which resulted in too thin body and unacceptable texture (Table 26). EXP #5 produced a product that was too thin, so no further testing was performed. No adverse syneresis was noticed in any of the yogurts.

TABLE 26

| | Yogurt texture and viscosity results | | |
|---|---|---|---|
| | Control stabilizer (AYS 79K) | Experimental 1 DE Common Corn hydrolyzed starch (EXP# 1) | Control 1 DE Common corn hydrolyzed starch (EXP# 28) |
| | Yogurt Vitex AYS 79K-1005 Gelatin Replacement, Hydrolyzed starch at 4.43% | | |
| Viscosity Day 1, cps | 16,240 | 15,488 | 6,960 |
| Viscosity Day 7, cps | 17,480 | 32,240 | 6,520 |
| Texture and Body | Good body and texture | Good body and texture, Hydrolyzed starch could be further reduced in the formulation | Too thin body, Unacceptable texture |

We claim:

1. A hydrolyzed waxy starch composition derived from waxy starch, wherein the hydrolyzed waxy starch has a dextrose equivalent (DE value) of greater than 0 to 3, a degree of polymerization (DP) between 126-6172 of >80%, an average molecular weight (mw) of <500 kDa, and wherein the composition forms a gel at 30% solids in aqueous medium; wherein the starch is corn starch, potato starch, tapioca starch, pea starch, or legume starch.

2. The hydrolyzed waxy starch composition of claim 1, wherein the composition has an opaque clarity indicated by a Hunter L value of >30, >40, >50, >60, >70, or >80.

3. The hydrolyzed waxy starch composition of claim 1, which has a gel strength at 30% solids in aqueous medium of >300 g, >400 g, >500 g, >600 g, >700 g, or >800 g.

4. The hydrolyzed waxy starch composition of claim 1, wherein the hydrolyzed waxy starch has a lower average molecular weight than a hydrolyzed starch with a similar DE produced by hydrolyzing waxy starch with α-amylase GC100.

5. The hydrolyzed waxy starch composition of claim 1, wherein a hydrolyzed starch with a similar DE produced by hydrolyzing waxy starch with α-amylase GC100 does not form a gel at 30% solids in aqueous medium.

6. A dairy composition comprising the hydrolyzed waxy starch composition of claim 1.

7. The waxy hydrolyzed starch composition of claim 1, wherein the waxy starch is waxy corn starch.

8. A hydrolyzed waxy starch composition derived from waxy starch, wherein the hydrolyzed waxy starch has a dextrose equivalent (DE value) of 11 to 14, a degree of polymerization (DP) between 25-45 of >29%, and an average molecular weight (mw) of <35 kDa.

9. The hydrolyzed waxy starch composition of claim 8, wherein the hydrolyzed waxy starch has a lower average molecular weight and/or a higher percentage of hydrolyzed starches with a DP between 25-45 than a hydrolyzed starch with a similar DE produced by hydrolyzing waxy starch with α-amylase GC100.

10. The hydrolyzed waxy starch composition of claim 8, wherein the starch is corn starch, potato starch, tapioca starch, pea starch, legume starch, or rich starch.

11. A dairy composition comprising the hydrolyzed waxy starch composition of claim 8.

12. The hydrolyzed waxy starch composition of claim 8, wherein the waxy starch is waxy corn starch.

13. A hydrolyzed waxy starch composition derived from waxy starch, wherein the hydrolyzed waxy starch has a dextrose equivalent (DE value) of 14 to 20, a degree of polymerization (DP) between 20-45 of >60%, and an average molecular weight (mw) of <10 kDa; wherein the starch is corn starch, potato starch, tapioca starch, pea starch, or legume starch.

14. The hydrolyzed starch composition of claim 13, wherein the hydrolyzed starch has a lower average molecular weight and/or a higher percentage of hydrolyzed starches with a DP between 20-45 than a hydrolyzed starch with a similar DE produced by hydrolyzing waxy starch with α-amylase GC100.

15. A dairy composition comprising the hydrolyzed waxy starch composition of claim 13.

16. The hydrolyzed waxy starch composition of claim 13, wherein the waxy starch is waxy corn starch.

\* \* \* \* \*

UNITED STATES PATENT AND TRADEMARK OFFICE
CERTIFICATE OF CORRECTION

PATENT NO. : 10,851,183 B2
APPLICATION NO. : 15/915323
DATED : December 1, 2020
INVENTOR(S) : Frank Derez et al.

Page 1 of 1

It is certified that error appears in the above-identified patent and that said Letters Patent is hereby corrected as shown below:

In the Specification

In Column 15, TABLE 7, under "CTRL 1956 (DE 8.2)", Line 1, delete "N" and insert -- NO --, therefor.

In Column 19, Line 29, delete "(100 $s^{-1}$ t 100 $s^{-1}$)" and insert -- (100 $s^{-1}$ to 100 $s^{-1}$) --, therefor.

In Column 22, Line 43, in "Example 5", Line 1, delete "Applications_of" and insert -- Applications of --, therefor.

Signed and Sealed this
Sixteenth Day of March, 2021

Drew Hirshfeld
*Performing the Functions and Duties of the*
*Under Secretary of Commerce for Intellectual Property and*
*Director of the United States Patent and Trademark Office*